США009393012B2

(12) United States Patent
DiPiero

(10) Patent No.: US 9,393,012 B2
(45) Date of Patent: Jul. 19, 2016

(54) SUTURE NEEDLE GUARD

(71) Applicant: Jennifer DiPiero, Cleveland, OH (US)

(72) Inventor: Jennifer DiPiero, Cleveland, OH (US)

( * ) Notice: Subject to any disclaimer, the term of this patent is extended or adjusted under 35 U.S.C. 154(b) by 479 days.

(21) Appl. No.: 13/888,763

(22) Filed: May 7, 2013

(65) Prior Publication Data

US 2014/0336678 A1 Nov. 13, 2014

(51) Int. Cl.
*A61B 17/04* (2006.01)
*A61B 17/06* (2006.01)

(52) U.S. Cl.
CPC ....... *A61B 17/0482* (2013.01); *A61B 17/06114* (2013.01); *A61B 17/0493* (2013.01); *A61B 2017/06142* (2013.01)

(58) Field of Classification Search
CPC .......... A61B 17/0482; A61B 17/0493; A61B 17/06114; A61B 2017/06142; A61M 5/3202
See application file for complete search history.

(56) References Cited

U.S. PATENT DOCUMENTS

| | | | |
|---|---|---|---|
| 3,944,069 A | | 3/1976 | Eldridge, Jr. |
| 4,610,667 A | * | 9/1986 | Pedicano ........... A61B 19/0288 604/192 |
| 4,735,311 A | * | 4/1988 | Lowe ................. A61M 5/3202 206/365 |
| 5,024,323 A | | 6/1991 | Bolton |
| 5,104,384 A | | 4/1992 | Parry |
| 5,358,102 A | * | 10/1994 | Brown ............. A61B 17/06138 206/227 |
| 5,617,952 A | | 4/1997 | Kranendonk |
| 5,836,920 A | | 11/1998 | Robertson |
| 6,595,955 B2 | | 7/2003 | Ferguson et al. |
| 7,316,668 B2 | | 1/2008 | Swenson |
| 7,927,314 B2 | | 4/2011 | Kuracina et al. |
| 2009/0005795 A1 | | 1/2009 | Giap |

* cited by examiner

*Primary Examiner* — Ashley Fishback
(74) *Attorney, Agent, or Firm* — Howard M. Cohn; Daniel M. Cohn

(57) ABSTRACT

A suture needle guard and method of operation for temporarily holding a suture needle during a surgical operation. The suture needle guard includes a hollow tube having a closed first end and an opposite, funnel shaped second end. The hollow tube has a hollow bore that extends from a closed bottom end to a funnel opening in the funnel shaped second end, and is configured to temporarily retain the suture needle within the suture needle guard. The suture needle guard also includes an immobilizing structure for temporarily immobilizing the suture needle guard during the surgical operation.

19 Claims, 5 Drawing Sheets

SUTURE NEEDLE GUARD

TECHNICAL FIELD OF THE INVENTION

The present invention relates generally to a suture needle guard for temporarily holding a suture needle during a surgical operation. More specifically, the present invention relates to a suture needle guard including a hollow tube having a hollow bore configured to temporarily retain the suture needle, and an immobilizing structure for temporarily immobilizing the suture needle guard during the surgical operation.

BACKGROUND OF THE INVENTION

Suture techniques are used within the medical community to promote the healing of deep tissue lacerations as well as wounds that are the result of surgery. What is employed almost exclusively in the medical community is a surgical needle with a suture swaged on the end of a needle. This needle is preferred to the older method in which a surgical needle had an eye at one end through which the suture was threaded. The prior configuration suffered from a larger profile at the eye end of the needle from the rest of the needle, thus requiring a larger opening to thread the suture through the wound.

Problems associated with inadvertent needle sticks have been identified as a serious health hazard and are well known in the art of blood sampling, percutaneous medication injection and other medical procedures involving use of medical sutures and needles. Disposable medical devices having piercing elements for administering a medication or withdrawing a fluid require safe and convenient handling. Significant attention has been focused on needle stick problems due to the contemporary sensitivity of exposure to AIDS, Hepatitis and other serious blood-borne diseases. On some occasions during a suturing session, the surgeon will pass a used suture needle and suture thread component to other associates in the operating room for disposal. This handling is a common cause of needle sticks which can be very dangerous to the surgeon, operating room personnel, and the patient. Further, many surgeons handle the suture needle with their fingers at certain points during the suturing process to change positions of the suture needle holder or particularly during the first stitch which must be locked with a knot. This too is a common point where needle sticks into the surgeon's fingers or patient can occur.

SUMMARY OF THE INVENTION

According to an embodiment of the present invention, there is disclosed a suture needle guard for temporarily holding a suture needle during a surgical operation. The suture needle guard includes a hollow tube having a closed first end and an opposite, funnel shaped second end. The hollow tube has a hollow bore that extends from a closed bottom end to a funnel opening in the funnel shaped second end, and is configured to temporarily retain the suture needle within the suture needle guard. The suture needle guard also includes an immobilizing structure for temporarily immobilizing the suture needle guard during the surgical operation.

According to another embodiment of the present invention, a method of temporarily holding a suture needle during a surgical operation is disclosed. The method includes providing a suture needle guard constructed of a hollow tube having a closed first end and an opposite, funnel shaped second end, the hollow tube having a hollow bore that extends from a closed bottom end to a funnel opening in the funnel shaped second end; temporarily retaining the suture needle within the suture needle guard; and temporarily immobilizing the suture needle guard during the surgical operation. The method also includes providing the hollow bore for receiving the suture needle with a curvature, and temporarily securing the suture needle within the hollow bore with a curvature. The method further includes inserting the suture needle within the hollow bore having a plug in the closed bottom end to grip the suture needle and temporarily secure the suture needle within the hollow bore. The method also includes inserting the suture needle within the hollow bore with a layer of flexible coating to grip the suture needle and temporarily secure the suture needle within the hollow bore. The method further includes inserting the suture needle within the hollow bore with a taper from the opening at an end of a substantially inner surface of the funnel shaped end to the closed bottom end of the hollow tube to temporarily secure the suture needle within the hollow bore. The method includes temporarily immobilizing the suture needle guard with a sheet of card stock to which the suture needle guard is secured, and temporarily affixing the sheet of card stock to the patient during a surgical operation.

According to another embodiment of the present invention, there is disclosed a suture needle guard kit for temporarily holding a suture needle during a surgical operation. The suture needle guard kit includes a sealed sterile pouch; a sheet for temporarily immobilizing the suture needle guard during the surgical operation; the suture needle guard being a hollow tube having a closed first end and an opposite, funnel shaped second end secured to the sheet; and the hollow tube having a hollow bore that extends from a closed bottom end to a funnel opening in the funnel shaped second end to temporarily retain the suture needle within the suture needle guard.

BRIEF DESCRIPTION OF THE DRAWINGS

The structure, operation, and advantages of the present invention will become further apparent upon consideration of the following description taken in conjunction with the accompanying figures (FIGs.). The figures are intended to be illustrative, not limiting. Certain elements in some of the figures may be omitted, or illustrated not-to-scale, for illustrative clarity. The cross-sectional views may be in the form of "slices", or "near-sighted" cross-sectional views, omitting certain background lines which would otherwise be visible in a "true" cross-sectional view, for illustrative clarity.

In the drawings accompanying the description that follows, both reference numerals and legends (labels, text descriptions) may be used to identify elements. If legends are provided, they are intended merely as an aid to the reader, and should not in any way be interpreted as limiting.

DETAILED DESCRIPTION OF THE PREFERRED EMBODIMENTS

Figure 1:
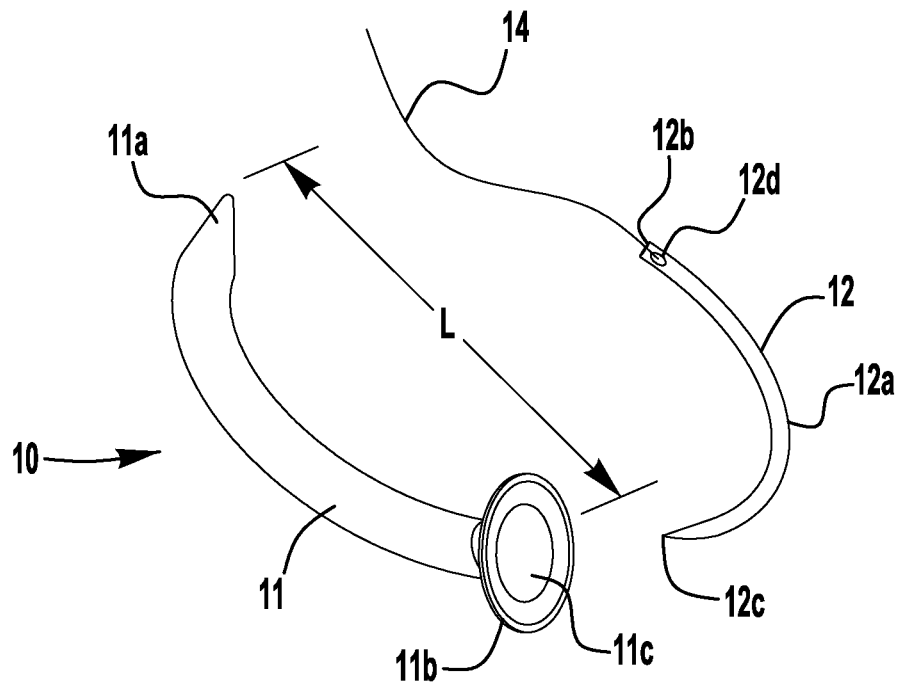
FIG. 1 is a front, three-dimensional view of a suture needle guard, in accordance with the present invention.

In the description that follows, numerous details are set forth in order to provide a thorough understanding of the present invention. It will be appreciated by those skilled in the art that variations of these specific details are possible while still achieving the results of the present invention. Well-known processing steps are generally not described in detail in order to avoid unnecessarily obfuscating the description of the present invention.

In the description that follows, exemplary dimensions may be presented for an illustrative embodiment of the invention. The dimensions should not be interpreted as limiting. They are included to provide a sense of proportion. Generally speaking, it is the relationship between various elements, where they are located, their contrasting compositions, and sometimes their relative sizes that is of significance.

In the drawings accompanying the description that follows, often both reference numerals and legends (labels, text descriptions) will be used to identify elements. If legends are provided, they are intended merely as an aid to the reader, and should not in any way be interpreted as limiting.

Many common medical procedures involve closing tissue by the use of sutures. A suture is a strand or fiber which holds previously opened tissue shut after the suture is driven through a patient's tissue with a suture needle. The suture process in its most simple form involves a suture needle, a suture, forceps, and a surgical needle holder. While working on living tissue, the suture and suture needle must at all times remain sterile to minimize the risk of infection to the patient. Further, the suture needle must be readily at hand for the surgeon's instant use during the operation. Therefore, the suture needle must be placed on a convenient sterile surface during an operation so that they may be readily accessed by the surgeon, while maintaining the sterility of the operating area. In addition, the surgeon must take care that he or she does not accidentally injure himself, other medical personnel, or the patient with a suture needle that has been used to suture tissue.

FIG. 1 illustrates the suture needle guard 10, designed to provide a sterile docking port for a suture needle 12 during a medical procedure. The suture needle guard 10 provides a sterile environment in which the surgeon or doctor may temporarily lodge the suture needle 12 during a medical procedure. Suture needle guard 10 provides an easily accessible but secured storage. It acts to create a sterile environment to store the suture needle 12, and also as a way to protect the surgeon or doctor, other medical personnel, and the patient from harmful and dangerous needle sticks. The doctor or surgeon will have a constant place to store the suture needle 12, so the suture needle will always be conveniently at hand and at the same location. Further, the suture needle guard 10 provides an easier and safer disposal method of the contaminated suture needle 12.

Suture needle guard 10 may be constructed of any appropriate material, such as a rubber or plastic polymer. Suture needle guard 10 consists of a conically shaped, hollow tube 11 with one end 11a closed and an opposite funnel shaped end 11b having an opening 11c. While suture needle guard 10 typically has a conical shape, any desired shape may be used. Further, it is within the terms of the embodiment that suture needle guard 10 has a curved shape to accommodate a curved suture needle 12, since standardized suture needles typically have a curved shape.

The overall length 1 from the closed end 11a to the opposite opening 11c in the funnel shaped end 11b may be a range between about 10 mm and about 30 mm. However, it is within the terms of the preferred embodiment that any length and diameter can be used to secure a suture needle as discussed herein.

The suture needle 12, which is to be temporarily secured within the suture needle guard 10, is a needle-like instrument with an extremely sharp point at one end and the suture 14 attached to its other end. The suture needle 12 generally includes a shaft 12a having a rear end portion 12b with an opening or eye 12d there through to secure the suture 14 and a sharp needle point 12c at a front end portion for puncturing skin and tissue through which the suture needle travels. Suture needles vary in size and shape, and the choice of a particular size or shape of suture needle is dictated by the type of medical procedure to be performed. Suturing needles are usually made from a cut blank of material such as stainless steel. The cut blank is metal-worked using well known machining techniques to form the suture needle 12.

Figure 3:
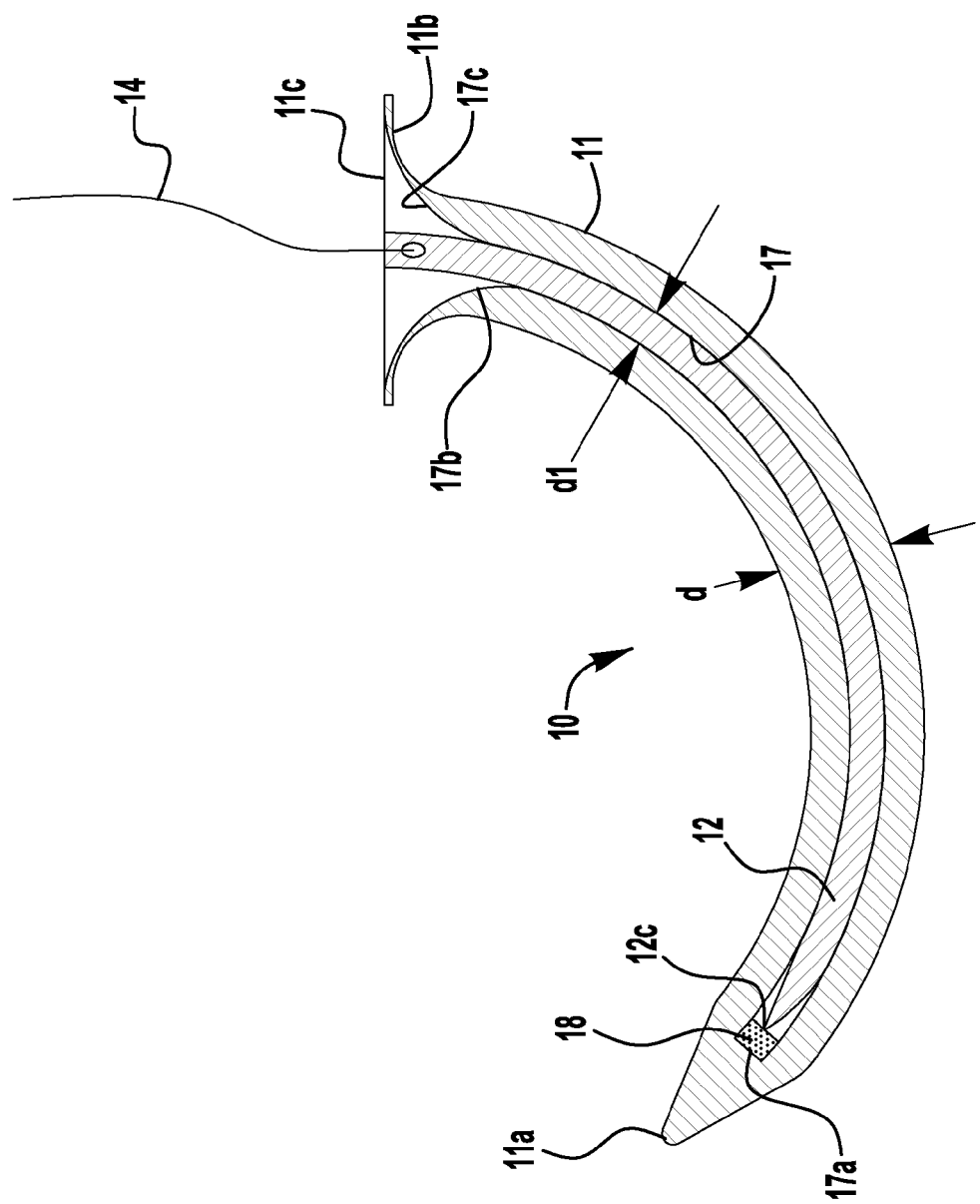
FIG. 3 is a cross-sectional view of a suture needle guard, in accordance with the present invention.

FIG. 3 illustrates a cross sectional view of the hollow tube 11 with the closed end 11a and funnel shaped end 11b. The hollow tube 11 has a hollow bore 17 which extends from the closed bottom end 17a to the funnel opening 11c. In one embodiment the hollow bore 17 has a constant diameter from the closed bottom end 17a to the small opening 17b at one end of the substantially conical inner surface 17c of the funnel shaped end 11b. The substantially conical inner surface 17c of the funnel shaped end 11b extends from the small opening 17b to the funnel opening 11c. It is within the terms of the embodiment that there be an antimicrobial or wetting agent that lines the hollow bore 17.

The length of the hollow bore 17 which extends from the closed bottom end 17a to the funnel opening 11c within the suture needle guard 10 may be a range between about 10 mm to about 30 mm. The inner diameter dl of the hollow bore 17 from the closed bottom end 17a to the small opening 17b can also be a range between about 10 mm to about 30 mm. However, it is within the terms of the preferred embodiment that any length and diameter can be used to secure a suture needle as discussed herein. The conical inner surface 17c may have a curvature as shown. As further shown in FIG. 3, a plug 18 of foam or similar cushioning material is disposed in the closed bottom end 17a of the hollow bore 17. The plug 18 functions to grip the needle point 12c and temporarily secures the needle 14 within the hollow bore 17 of the suture needle guard 10 until the doctor or surgeon removes it. It is also within the terms of the preferred embodiment to construct the suture needle guard 10 without the plug 18.

Figure 2:
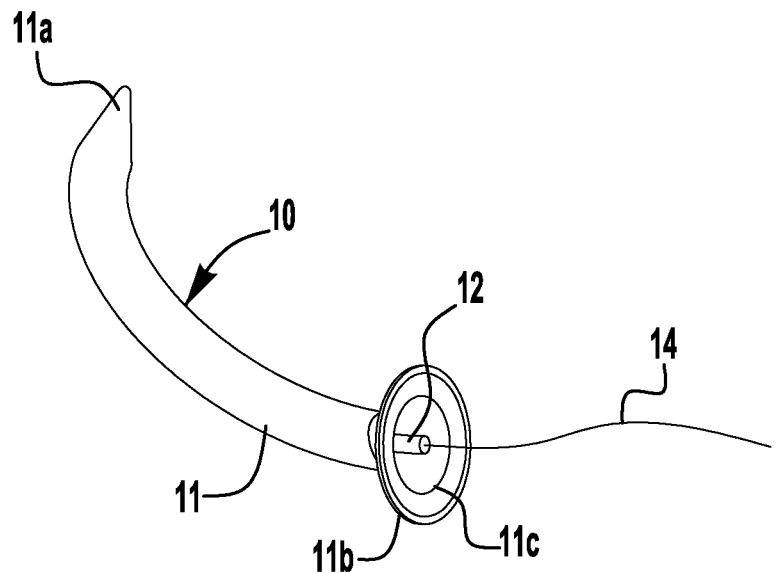
FIG. 2 is a front, three-dimensional view of a suture needle secured within the suture needle guard, in accordance with the present invention.

The funnel opening 11c must be large enough to comfortably allow the doctor or surgeon to easily locate and place the suture needle 12 there through, even when wearing cumbersome gloves. FIG. 2 illustrates the suture needle 12 extending through the opening 11c of the funnel shaped end 11b and temporarily secured within the hollow bore 17 which extends from the closed bottom end 17a to the funnel opening 11c.

Figure 3A:
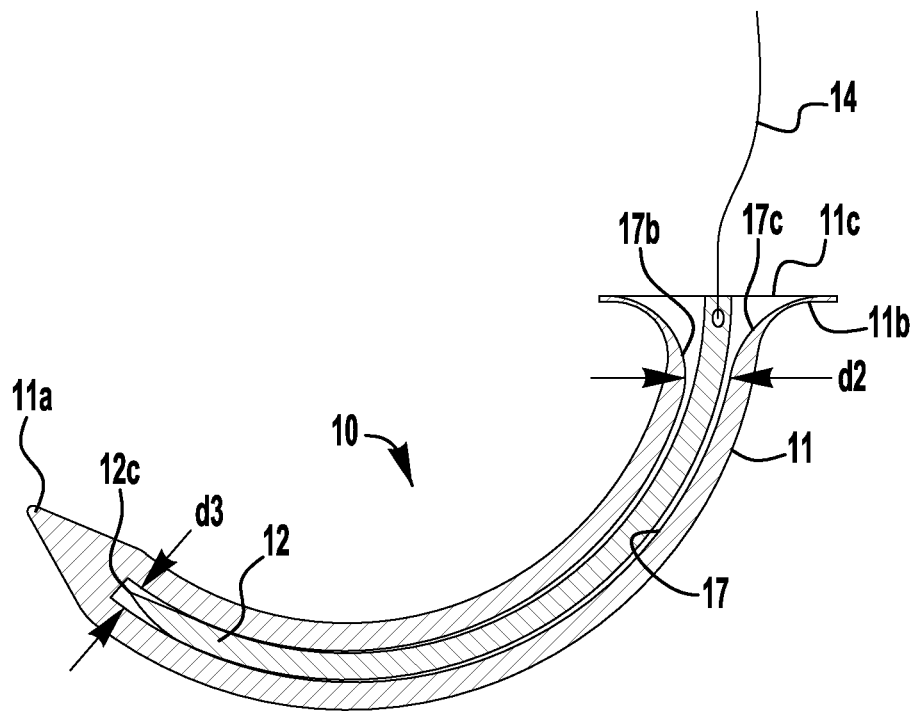
FIG. 3a is a cross-sectional view of a suture needle guard with a tapered hollow bore, in accordance with the present invention.

In an alternative embodiment, as shown in FIG. 3a, the hollow bore 17 from the closed bottom end 17a to the small opening 17b is preferably tapered from the small opening 17b having a diameter d2 to the closed bottom end 17a having a diameter d3 smaller than d2 so that the pressure created by the tapering effect of the hollow bore 17 against the suture needle 12 would act to temporarily secure the suture needle 12 within the suture needle guard 10.

Figure 3B:
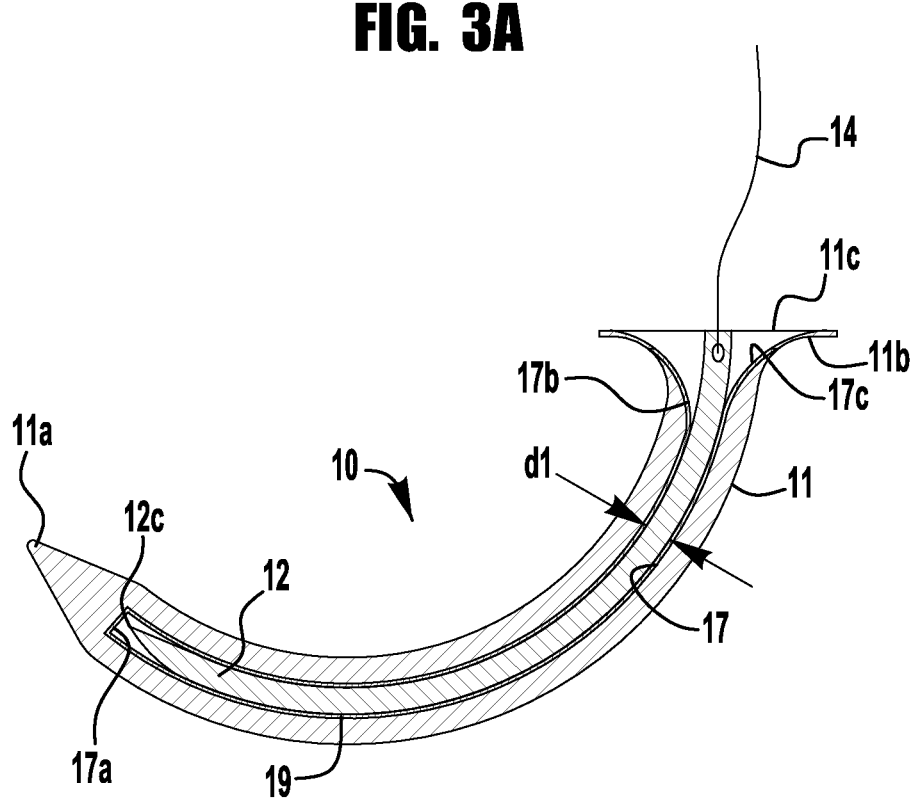
FIG. 3b is a cross-sectional view of a suture needle guard with a layer of flexible coating extending within the hollow bore, in accordance with the present invention.

In an alternative embodiment, as shown in FIG. 3b, a layer of flexible coating 19 would extend within the hollow bore 17 from the closed bottom end 17a to the funnel opening 11c. The purpose of flexible coating 19 would be to create pressure against the suture needle 12 as it is inserted into the suture needle guard 10 to temporarily secure the suture needle 12 within the suture needle guard 10.

Figure 4:
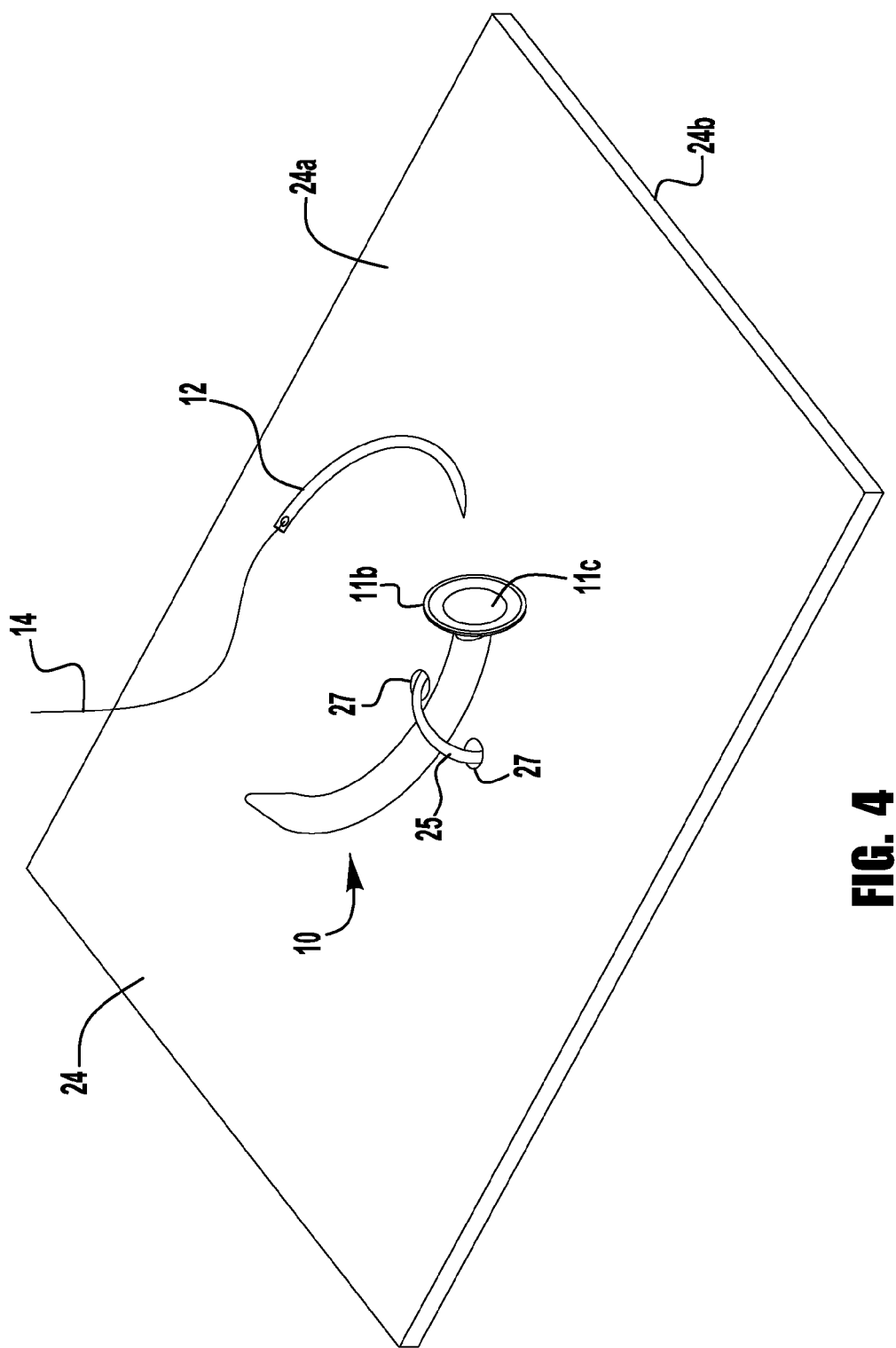
FIG. 4 is a front, three-dimensional view of a suture needle guard secured to a sheet of card stock with a suture needle and suture, in accordance with the present invention.

FIG. 4 illustrates an embodiment in which the suture needle guard 10 includes an immobilizing structure for temporarily immobilizing the suture needle guard during the surgical operation. The immobilizing structure is a sheet 24 of card stock to which the suture needle guard 10 is secured. The card stock may be constructed of any type of desired material, such as paper, plastic or metal. Preferably the suture needle guard 10 is secured to an upper side 24a of sheet 24 of card stock. It is within the terms of the preferred embodiment that the suture needle guard 10 be secured to the upper side 24a of sheet 24 by various means such as a band or cable 25 of plastic, rubber or twist tie material can extend over the hollow tube 11 and through two spaced holes 27 through the sheet so that the ends of the band or cable can be secured together on the underside 24b. It is further within the terms of the embodiment that there be guide grooves (not shown) on the upper side 24a of sheet 24 to allow the suture needle guard 10 to easily slip under the band or cable 25. Further, material such as silicone may be added to the upper side 24a of sheet 24 to add additional grip to further immobilize the suture needle guard 10. The suture needle guard 10 can be secured to the upper side 24a of sheet 24 by bonding the suture needle guard 10 with an adhesive or providing a band or cable 25 about the hollow tube 11 and bonding the band or cable to the upper side 24a of sheet 24 with an adhesive.

In use, the sheet 24 provides both a carrier for the suture needle guard 10, as well as a platform to temporarily secure the suture needle guard to the patient during use of the suture needle 12. To this end, there may be an adhesive on the underside 24b of sheet 24 to temporarily attach the suture needle guard 10 to the patient for convenience. Alternatively, any other method of attaching sheet 24 may be used, such as a Velcro strap (not shown) to be attached the sheet card stock and affixed to the patient.

Figure 5:
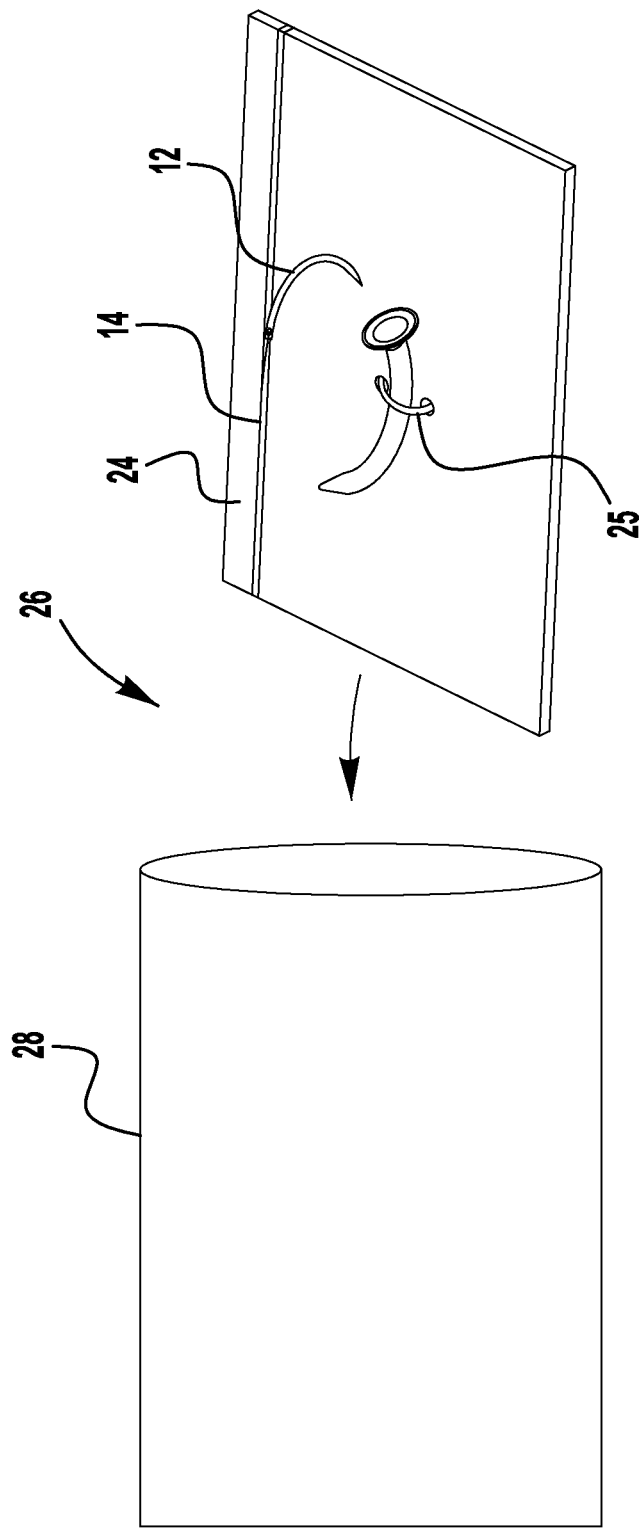
FIG. 5 is a front, three-dimensional view of a suture needle guard kit, including a sealed sterile pouch and a suture needle guard secured to a sheet of card stock with a suture needle and suture, in accordance with the present invention.

It is within the terms of the embodiment that the suture needle guard 10 be sold as a kit 26 as shown in FIG. 5. In this embodiment, a sealed sterile pouch 28 will contain the sheet 24 of card stock with the suture needle guard 10 secured thereto, such as by the band or cable 25. A suture needle 12 and suture 14 can be secured to the sheet 24 by placing the needle on the upper side 24a of sheet 24 and winding the suture 24 around the card as seen in FIG. 5.

It is also within the terms of the embodiment that the kit 26 includes forceps and a needle holder (not shown) so that kit 26 would conveniently contain all the elements required by the doctor or surgeon. Further, when conducting a surgical procedure, the sheet 24 provides both a housing for the suture needle guard 10, as well as a platform to temporarily secure the suture needle to the patient, as discussed above.

In general suturing operation, the suture 14 is tied through the aperture 12d in the rear portion 12b of the suture needle 12. The suture needle guard 10 may be utilized as a convenient temporary storage location during the tying process. Once the doctor or surgeon is ready to begin the suture, the suture needle 12 is grasped by the needle holder (not shown) at the rear portion 12b, and driven through the patient's tissue. Subsequent to this first step, the suture needle 12 is then released and regrasped on the other side of the tissue, at a position adjacent to the needle tip 1cb. So engaged, the suture needle 12 is then pulled through the tissue, threading the suture 14 through the wound. Meanwhile, forceps are held in the other hand to manipulate tissue during the suture process, and to hold the suture needle 12 when released by the needle holder.

Once the suture needle 12 and suture 14 are through the tissue in the first half of a suture, it is necessary to either drop the suture needle from the needle holder or pass it to an engagement between the tongs of a pair of forceps in order to appropriately grasp the needle to replace it into the loaded position again to repeat the first step. At this point, the suture needle 12 may be passed through the opening 11c of the suture needle guard 10 and temporarily secured therein, as discussed above.

Although the invention has been shown and described with respect to a certain preferred embodiment or embodiments, certain equivalent alterations and modifications will occur to others skilled in the art upon the reading and understanding of this specification and the annexed drawings. In particular regard to the various functions performed by the above described components (assemblies, devices, etc.) the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

The invention claimed is:

1. A suture needle guard for temporarily holding a curved suture needle having a rear portion with a suture secured thereto at one end and a sharp point at an other end during and after a surgical operation, comprising:
   a hollow tube having a closed first end and an opposite, funnel shaped open second end;
   the hollow tube having a hollow bore that extends from a closed bottom end to a funnel opening in the funnel shaped open second end;
   the hollow tube being configured to temporarily retain the suture needle within the suture needle guard; and
   a sheet of card stock having the suture needle guard secured thereto for temporarily immobilizing the suture needle guard during the surgical operation without covering or prohibiting delivery of the curved suture needle into the funnel shaped open second end.

2. The suture needle guard of claim 1 wherein the hollow bore of the hollow tube has a curvature for receiving the suture needle and temporarily securing the suture needle within the hollow bore.

3. The suture needle guard of claim 1 wherein the hollow bore of the hollow tube has a plug in the closed bottom end to grip the suture needle and temporarily secure the suture needle within the hollow bore.

4. The suture needle guard of claim 3 wherein the plug in constructed of a cushioning material.

5. The suture needle guard of claim 1 wherein the hollow bore has a constant diameter from the closed bottom end to an opening at an end of a substantially conical inner surface of the funnel shaped open second end.

6. The suture needle guard of claim 1 wherein the hollow bore has a layer of flexible coating extending from the closed bottom end to the funnel opening of the hollow bore to temporarily secure the suture needle within the hollow bore.

7. The suture needle guard of claim 1 wherein the hollow bore is tapered from the opening at an end of a substantially conical inner surface of the funnel shaped open second end to the closed bottom end of the hollow tube to temporarily secure the suture needle within the hollow bore.

8. The suture needle guard of claim 1 wherein the suture needle guard is secured to the sheet of card stock with a structure selected from the group consisting essentially of an adhesive and a cable.

9. The suture needle guard of claim 8 wherein the sheet of card stock is configured to be temporarily affixed during a surgical operation.

10. The suture needle guard of claim 1 wherein the hollow tube is conically shaped.

11. A method of temporarily holding a curved suture needle having a rear portion with a suture secured thereto at one end and a sharp point at an other end during a surgical operation, comprising:
providing a curved suture needle guard constructed of a hollow tube having a closed first end and an opposite, funnel shaped open second end, the hollow tube having a hollow bore that extends from a closed bottom end to a funnel opening in the funnel shaped open second end;
temporarily retaining the curved suture needle within the suture needle guard; and
temporarily immobilizing the suture needle guard during the surgical operation.

12. The method of claim 11 including:
providing the hollow bore for receiving the suture needle with a curvature; and
temporarily securing the suture needle within the hollow bore with a curvature.

13. The method of claim 11 including:
inserting the suture needle within the hollow bore having a plug in the closed bottom end to grip the suture needle and temporarily secure the suture needle within the hollow bore.

14. The method of claim 11 including inserting the curved suture needle within the hollow bore having a layer of flexible coating to grip the curved suture needle and temporarily secure the curved suture needle within the hollow bore.

15. The method of claim 11 including inserting the curved suture needle within the hollow bore with a taper from the opening at an end of a substantially inner surface of the funnel shaped open second end to the closed bottom end of the hollow tube to temporarily secure the curved suture needle within the hollow bore.

16. The method of claim 11 including temporarily immobilizing the suture needle guard with a sheet of card stock to which the suture needle guard is secured.

17. The method of claim 16 including temporarily affixing the sheet of card stock during a surgical operation.

18. A suture needle guard kit for temporarily holding a curved suture needle having a rear portion with a suture secured thereto at one end and a sharp point at an other end during a surgical operation, comprising:
a suture needle guard being a hollow tube having a closed first end and an opposite, funnel shaped open second end;
a sealed sterile pouch;
a sheet for temporarily immobilizing the suture needle guard during the surgical operation without covering or prohibiting delivery of the curved suture needle into the funnel shaped open second end;
the suture needle guard being secured to the sheet; and
the hollow tube having a hollow bore that extends from a closed bottom end to a funnel opening in the funnel shaped open second end to temporarily retain the curved suture needle within the suture needle guard.

19. The suture needle guard kit of claim 18 wherein:
the sheet for temporarily immobilizing the suture needle guard during the surgical operation is a sheet of card stock to which the suture needle guard is secured.

* * * * *